(12) United States Patent
Weinstock

(10) Patent No.: US 7,640,052 B2
(45) Date of Patent: Dec. 29, 2009

(54) METHOD OF INTEGRATED PROTON BEAM AND THERAPEUTIC MAGNETIC RESONANCE THERAPY

(75) Inventor: Ronald J. Weinstock, Corona Del Mar, CA (US)

(73) Assignee: IPPP, LLC, Pompano Beach, FL (US)

( * ) Notice: Subject to any disclaimer, the term of this patent is extended or adjusted under 35 U.S.C. 154(b) by 0 days.

(21) Appl. No.: 11/824,975

(22) Filed: Jul. 2, 2007

(65) Prior Publication Data
US 2008/0269593 A1    Oct. 30, 2008

Related U.S. Application Data

(63) Continuation-in-part of application No. 10/856,632, filed on May 28, 2004.

(51) Int. Cl.
*A61B 5/05* (2006.01)

(52) U.S. Cl. .................... 600/407; 600/410; 600/411; 600/431; 606/32

(58) Field of Classification Search ................. 600/407, 600/410, 411–423, 431; 324/316; 378/64, 378/65, 147, 149, 150; 424/9.33; 606/32
See application file for complete search history.

(56) References Cited

U.S. PATENT DOCUMENTS

| | | | | |
|---|---|---|---|---|
| 5,592,086 | A * | 1/1997 | Weinstock et al. | 324/318 |
| 6,366,798 | B2 * | 4/2002 | Green | 600/411 |
| 7,082,325 | B2 * | 7/2006 | Hashimshony et al. | 600/411 |
| 7,194,063 | B2 | 3/2007 | Dilmanian et al. | |
| 2005/0197564 | A1 * | 9/2005 | Dempsey | 600/411 |
| 2008/0270517 | A1 * | 10/2008 | Baumann et al. | 709/202 |

* cited by examiner

Primary Examiner—Brian Casler
Assistant Examiner—Joel M Lamprecht
(74) Attorney, Agent, or Firm—Melvin K. Silverman; Yi Li

(57) ABSTRACT

A method of therapeutic treatment including the steps of modulated application of a time domain radiation beam to a therapeutic target; and providing a time domain application of a modulated magnetic resonance (MR) signal to the therapeutic target during the periods of application out-of-phase with energy peaks of the radiation beam.

4 Claims, 18 Drawing Sheets

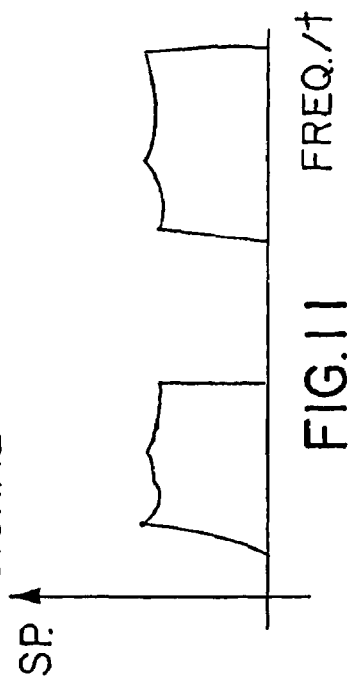
FIG. 11 UNHEALTHY SIGNAL
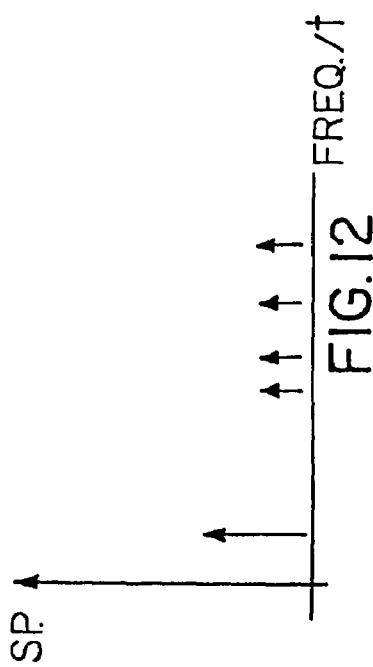
FIG. 12
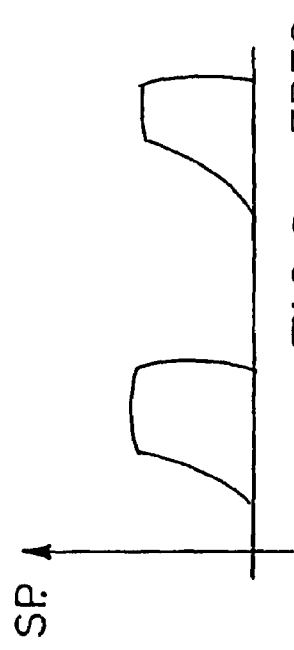
FIG. 9 HEALTHY SIGNAL
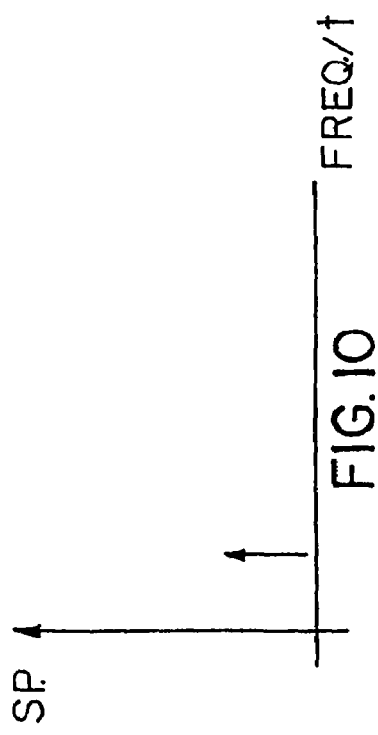
FIG. 10

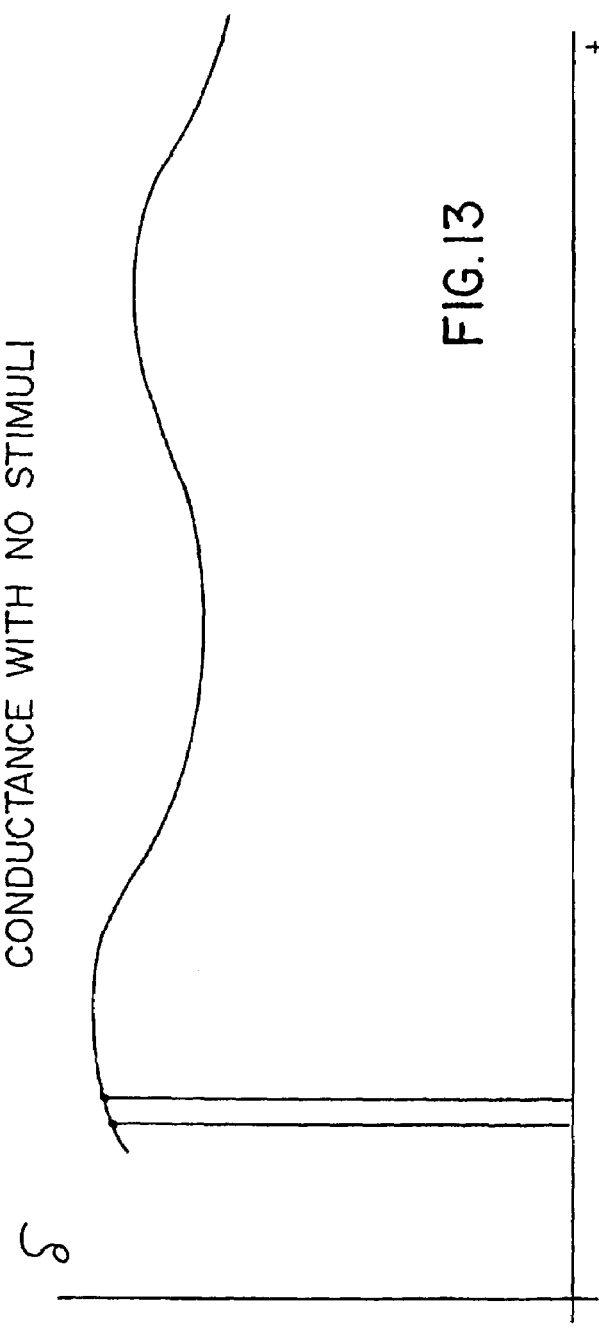
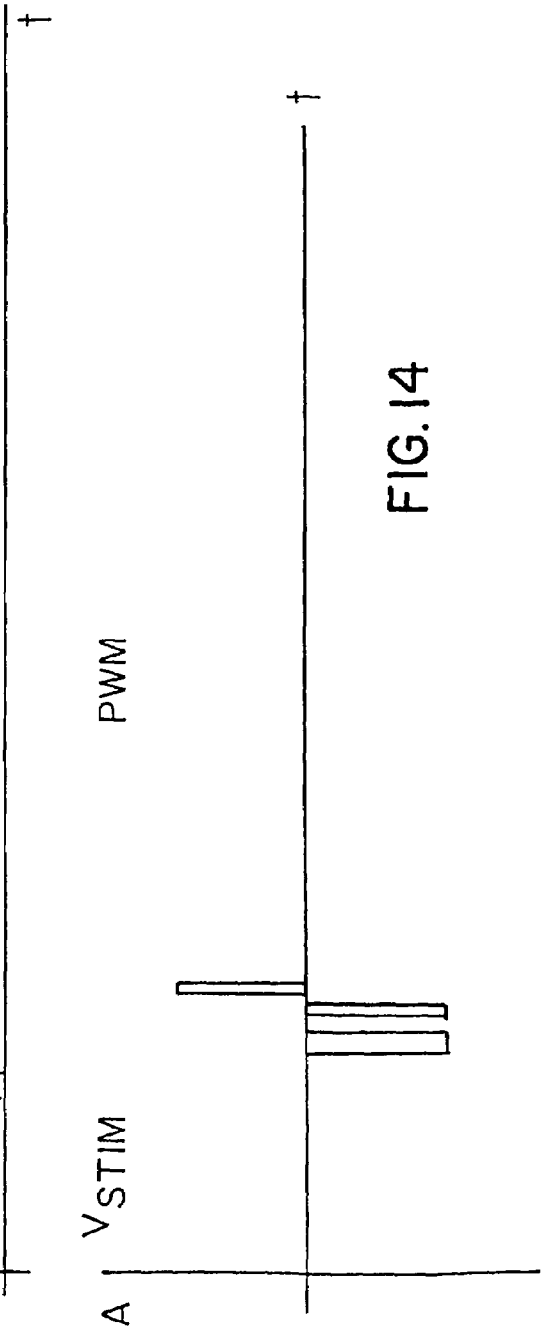
FIG. 13
FIG. 14

METHOD OF INTEGRATED PROTON BEAM AND THERAPEUTIC MAGNETIC RESONANCE THERAPY

CROSS REFERENCE TO RELATED APPLICATION

This application is a continuation-in-part application of co-pending patent application Ser. No. 10/856,632, entitled System for Analyzing and Treating Abnormality of Human and Animal Tissues, filed May 28, 2004. Said application is incorporated by reference in its entirety.

FIELD OF THE INVENTION

The present invention relates generally to methods for performing microbeam X-ray and proton radiation, primarily for cancer tumor treatment, however integrated with in vivo or ex vivo arrays of nuclear or electron magnetic resonant electromagnetic waves, to limit the beam effect within the tumor by decreasing the level of X-ray or proton radiation otherwise required in a given procedure. The invention is also applicable to the treatment of Parkinson's tremors and other uses with a gamma knife. Another possible effect use in on is beam ionic movement in such a way that a portion beam is more effective to the treatment target.

BACKGROUND OF THE INVENTION

Conventional treatment of malignant conditions by such as surgery, chemotherapy and radiation therapy have exhibited favorable results in many cases, while failing to be completely or satisfactorily effective in all cases. However, a historic and continuing problem and limitation in radiation therapy has been to maximize the so-called therapeutic index, defined as the ratio of maximum tolerable dose to the dose at which unacceptable levels of normal tissue toxicity occur, that is, to determine or establish a minimum dose required for effective tumor control. This goal however has proven particularly difficult to achieve in treating a variety of cancers including those of the central nervous system, liver and various types of metastatic tumors.

Notwithstanding the general issue of toxicity, the treatment rate of metastic tumors of the spinal cord and brain have not improved appreciably in several years, using conventional surgical techniques and proton beam therapy. This is because dosage that can be delivered to malignant CNS tumors is limited by the tolerance of normal brain of spinal cord to radiation. Recently, the concepts of microbeam radiation, grid radiation, and spatial fractionalization of X-rays for therapeutic purposes have appeared. This proved helpful in various clinical settings, for example, treatment of prostate cancer. Three-dimensional imaging, taken in combination with micro-beam radiation, enables proton treatment to be more advantageously directed than in the past. X-rays have also been lacking as a solution in the treatment of malignancies at a skin or tissue surface because conventional X-rays, due to their lack of a charge and mass, result dissipation of their energy at or near the surface of the tissue of interest and also are more prone to scattering of undesirable energy beyond the cancer site. This undesirable pattern of energy placement is also a problem in proton beam therapy and can result in unnecessary damage to healthy tissue, often preventing physicians from use of sufficient radiation to effectively control the cancer.

Proton beam strategies include the treatment or doping of the malignant tissue with a contrast agent which, because of the electron shell structure of the dopant will increase the amount of the target dose absorbed by the target tissue, this method commonly referred to as photon activation therapy.

Recently, the concept of bi-directional interlaced microbeam radiation therapy (BIMRT) (see U.S. Pat. No. 7,194, 063 (2007) to Dilmanian, et al entitled Methods for Implementing Microbeam Radiation Therapy appeared in the art. The teaching of Dilmanian is that of the use of intersecting and non-intersecting arrays of photon or x-ray microbeams, that is, the use of two spatially distinct microbeam paths together with, preferably, a third microbeam path. The first and second microbeam paths may be interleaved with each other, while the third microbeam path is angularly rotated and laterally translated with respect to the first and second paths. The teaching however of Dilmanian, and other art known to the inventor, is still that of the use of a single form of electromagnetic radiation, however larger in number the beams or microbeams which co-act with each other, whether with or without the use of contrast to assist in the "targeting" of the tumor of interest.

The instant invention is a departure from the above and other know art in its concurrent use, either in vivo or ex vivo (prior to tumor contact) of nuclear or electron resonant electromagnet resonance with known X-ray and photon beam therapies of various types.

SUMMARY OF THE INVENTION

The present invention relates to the concurrent treatment of malignant tissue with a nuclear or electron magnetic resonance signal and standard proton or X-ray radiation therapy.

It is an object of the invention to improve the effectiveness of X-ray and proton beam therapy while reducing the toxicity thereof.

It is another object to enhance the utility and effectiveness of gamma knife surgery.

The above and yet other objects and advantages of the present invention will become apparent from the hereinafter set forth Brief Description of the Drawings, Detailed Description of the Invention and Claims appended herewith.

BRIEF DESCRIPTION OF THE DRAWINGS

FIGS. 9 and 10 are respective and resonance peak waveforms of a healthy tissue.

FIGS. 11 and 12 are respective signals and spectra waveforms of an abnormal tissue such as that subject to treatment herein.

FIGS. 13 and 14 are respective signals and EMR peak spectra diagrams showing the treatment wave delivery to the therapy target.

DETAILED DESCRIPTION OF THE INVENTION

Figure 1:
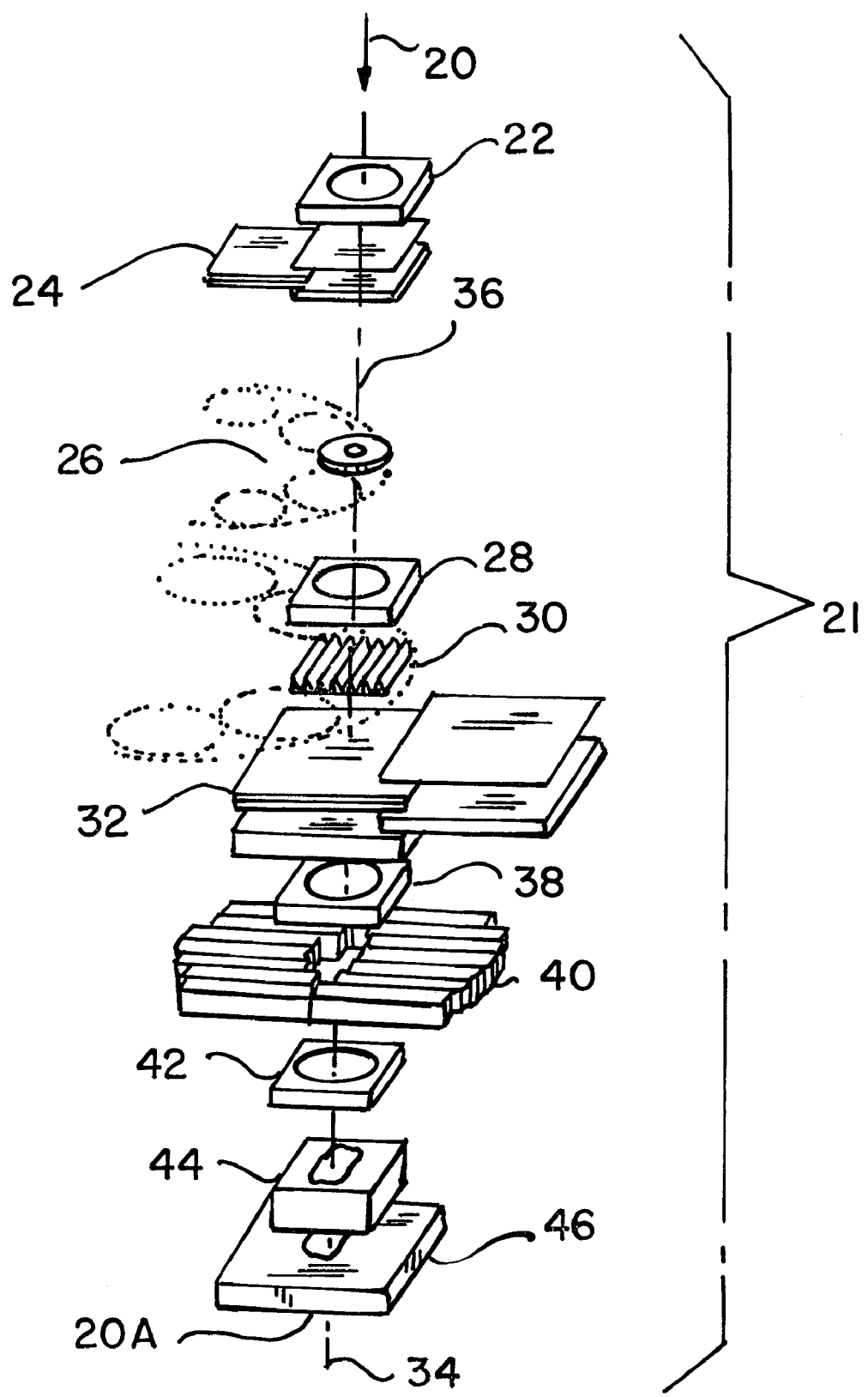
FIG. 1 is a schematic view of a proton beam delivery system of the double scattering type.

With reference to the schematic view of FIG. 1, there is shown a typical prior art proton beam delivery system 21 of the scattering method type. Systems of this type, which have been known since at least 2001 include a proton source 20 (see Background of the Invention), a precision profile monitor 22, a binary type first scattering plane 24, a second scattering elements 26, a first dose monitor 28, a ridge filter 30, and a range shifter 32. The lines phantom show the spatial adjustability of the second element 26, first dose monitor 28 and ridge filter 30. A goal of proton beams scattering is to cause the beam 20 to spread in a transverse plane to widen the therapeutic target area, i.e., isocenter 34. An axis of the entire system is as an irradiation axis 36. The thickness of first scattering plane 24 and material of the second element 26 control the respective energies delivered by the system which, typically, are in a range of 125 to 250 Mev. Range shifter 32 is followed by a flatness monitor 38 which monitors beam flatness to obtain homogenous energy at the isocenter 34 of a target 50. See FIG. 2. Typically, the maximum usable irradiation field is a circular region of 20 cm in diameter, having a maximum depth of about 30 g/cm2. To accomplish such adjustment in the energy, the ridge filter 30 is used to accomplish shifts in the depth of treatment in a range of 0 to about 125 mm water equivalents in step sizes of 1 mm each. Ridge filter 30 employs an array of metallic bars such that protons passing through bars of different thicknesses, produce Bragg peaks at different treatment depths.

Following flatness monitor 38 is collimator 40, energy monitor 42, bolus 44, (a range compensator) and patient collimator 46. The functions of collimators 40 and 46 are to direct the maximum proton energy in a lateral plane to best conform to the configuration of a tumor or tissue to be treated.

Figure 2:
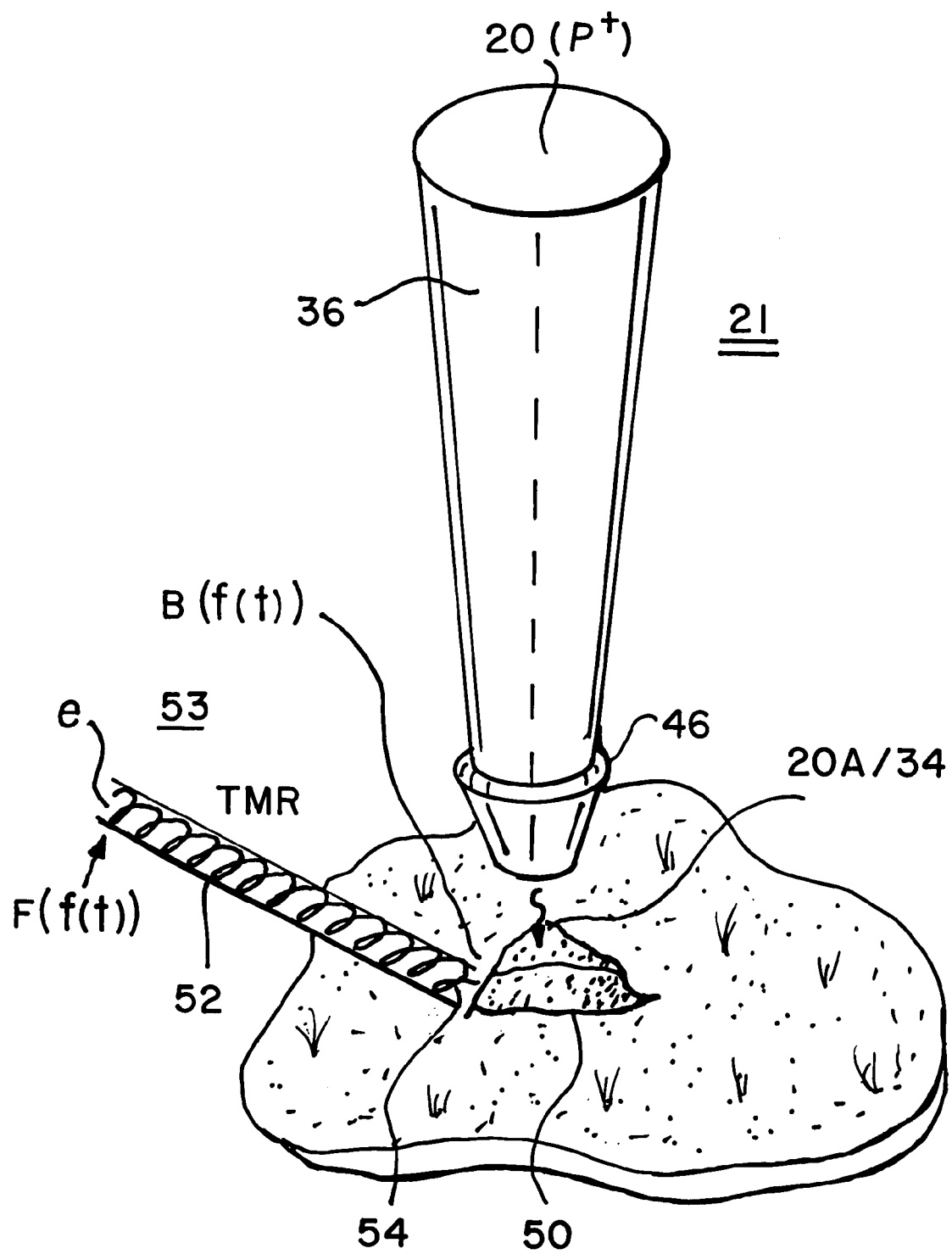
FIG. 2 is a schematic view showing the inventive method of combining therapeutic magnetic resonance (TMR) with proton beam therapy of a system of the type shown in FIG. 1.

Schematically shown in FIG. 2 is the entire assembly 21 of FIG. 1, this including the proton beam source 20, the irradiation axis 36, the isocenter 34, and treatment target 50. Laterally shown to the lower left of FIG. 2 is a therapeutic magnetic resonance (TMR) signal assembly 53 directed to therapeutic target 50. It is to be understood that this input may encompass both electron magnetic resonance (EMR) as taught in my said U.S. application Ser. No. 10/856,652 or nuclear magnetic resonance (NMR) of a more conventional type. In the schematic of in FIG. 2 is shown a toroidal coil 52 through which electrons pass on a time domain basis (as is more fully set forth below), thereby generating a time domain and spatial magnetic signal along the axis of the toroid, producing an output B(f(t)) at the target 50. The time domain relationship between proton output 20A of system 21 and the EMR signal output 54 of the coil 52 is shown in the block diagrammatic view of FIG. 3. Therefrom, it may be appreciated that a salient aspect of the present invention is to provide a reduced energy protons beam 20A at a time domain phase offset from that of the magnetic signal 54 resultant of the TMR coil 52. This may be noted by the respective sinusoidal patterns shown in FIG. 3 wherein the energy peaks of proton beam 20A are 180 degrees out of phase with those of the magnetic signal output 54 of the TMR assembly 53, the result being that reduced proton beam energy may be employed during the negative or off periods of the TMR assembly 53, and vice versa due to the inherent therapeutic effects of TMR (more fully discussed below and in my said pending application). A reduced level of proton, as well as X-ray, if that is the mode of treatment, energy is thus required to achieve a comparable or improved therapeutic result, an additional benefit thereof being reduction in damage to healthy tissue in the target region.

As may be appreciated, many other waveforms and combinations thereof of both the proton or x-ray beam 20A, or periods of intermittency between signal of the one treatment modality relative to the other will become apparent, upon experimentation, to those of ordinary skill in the art.

Figure 3:
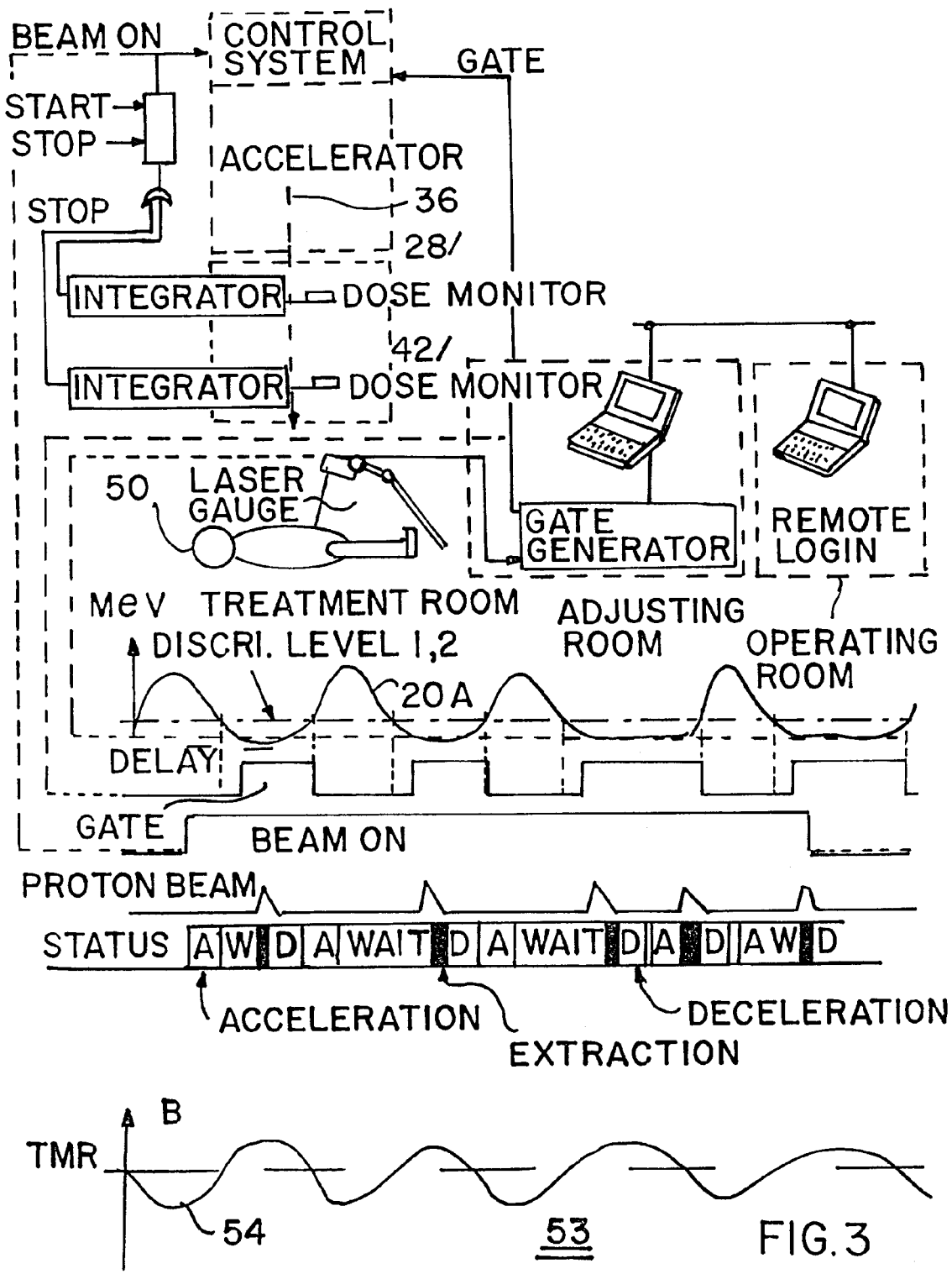
FIG. 3 is a flow diagram view of a dose control assembly of the system of FIG. 1 and showing the phase displacement of application of the TMR signal from the proton beam.

FIG. 3 is a flow diagram of the dose control assembly of FIG. 1.

Figure 4:
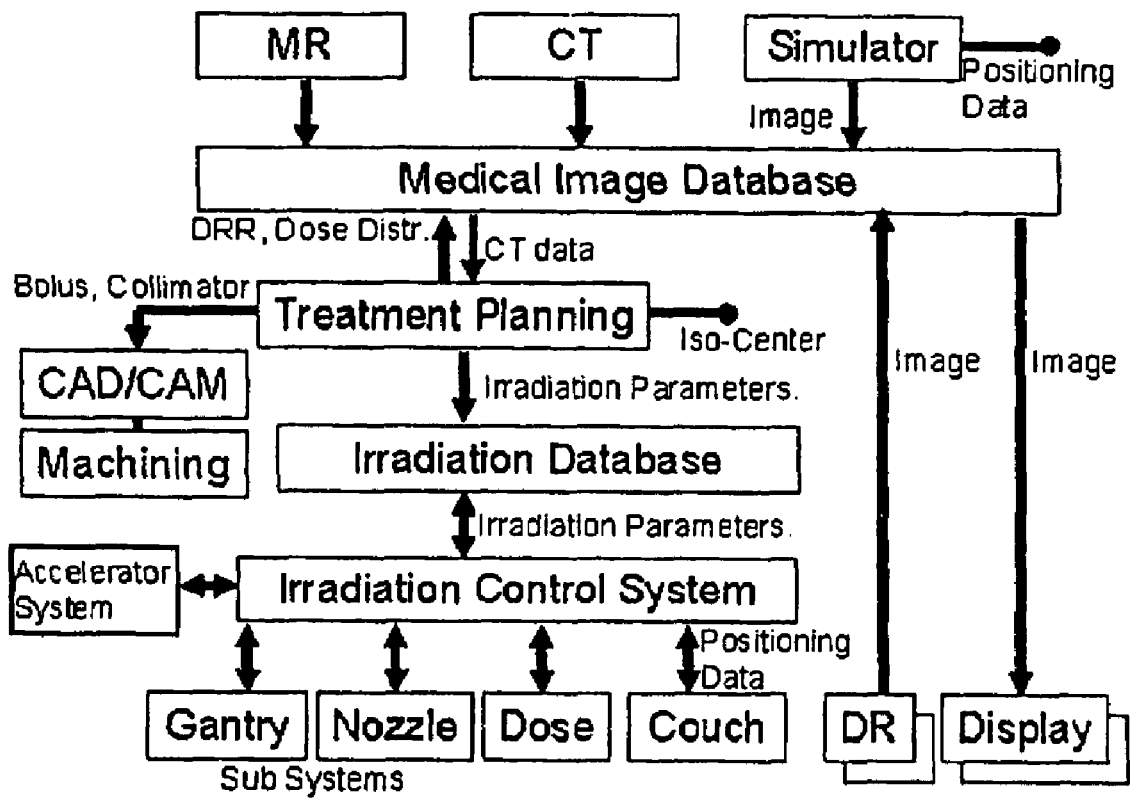
FIG. 4 is a flow diagram view of a radiation control of the system shown in FIGS. 1-3.
Figure 7:
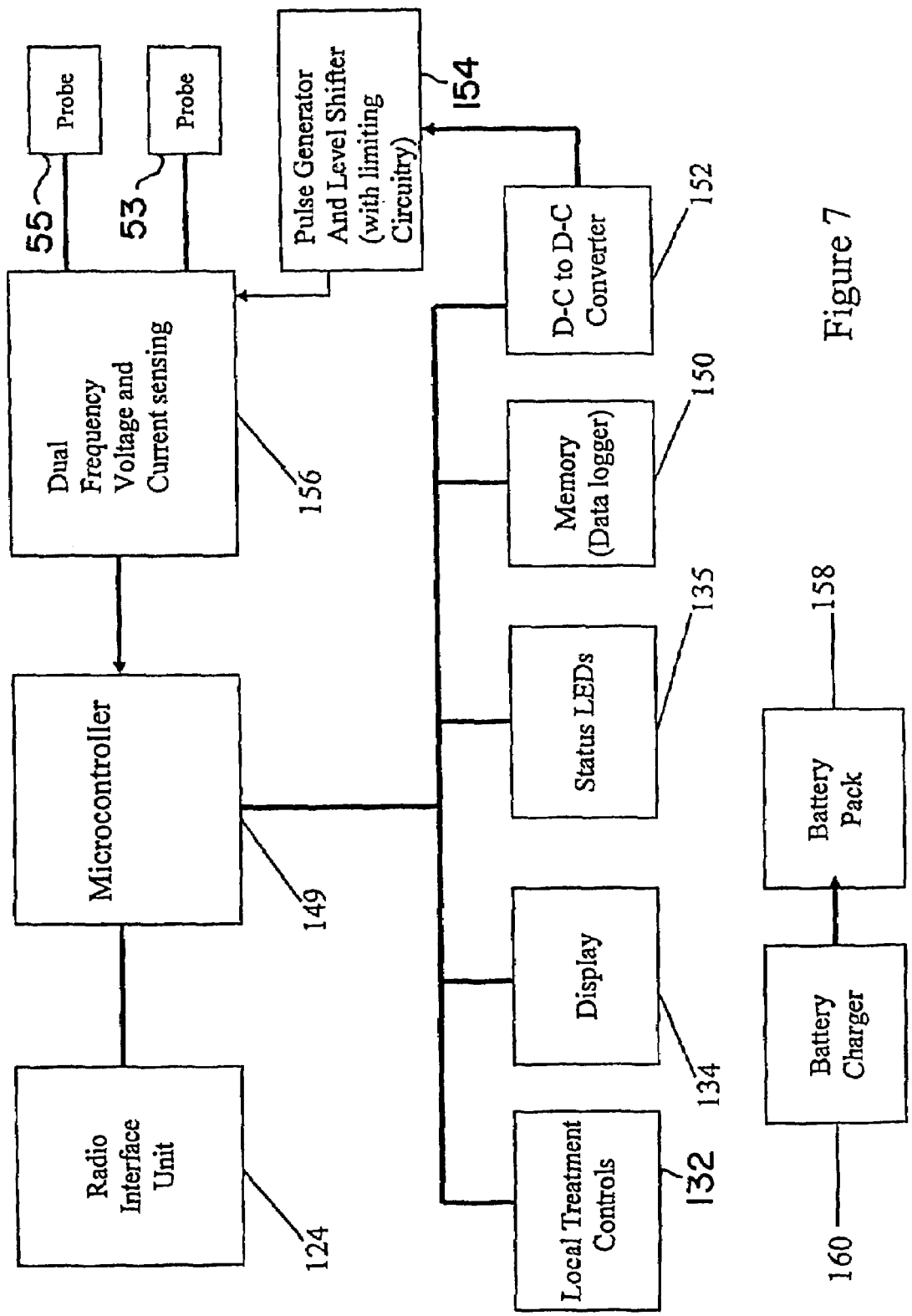
FIG. 7 is a block diagram view showing TMR comprising an electron magnetic resonance (EMR) portion of the system used to generate the wave shown at the bottom left of FIG. 3.

In FIG. 4 is shown a typical irradiation control center for the system shown and described with reference to FIGS. 1-3. Therefrom, it may be appreciated that, prior to therapy, irradiation parameters of the equipment are set in accordance with the process flow shown in FIG. 4. More particularly, the medical image database includes images from prior or contemporaneous magnetic imagining (MRI), computing tomography (TC), X-ray imaging, real time digital radiography (DR), and a treatment planning function. It may also include gamma knife and sterostatic imaging. The radiation database controls the planning data and the parameters for use of radiation of the accelerator. From the flow diagram of FIG. 4, it may be readily appreciated that the controls necessary to integrate the present invention into that of the prior art are relatively straightforward in terms of contemporary electronics and control technology. A block diagram of the TMR assembly 51 is shown in FIG. 7 and described below. By creating more ionic movement in tissue, tissue is able to absorb more of the beam energy with less power. The gamma knife application enables knifeless brain surgery and consists of a helmet with 144 focuses holes in which the X-ray or proton beam converges at a central point determined by 3D stereotatic imagining. Each beam is weak itself but where they converge they are hot enough to kill the tumor. The 3D imaging allows the hot convergence point to follow the contours of the tumor. One can apply TMR to these beams or use the sterotatic 3D imaging to guide the TMR beams as well using the various angles to the X-ray or proton beam as described in the current art.

Figure 5:
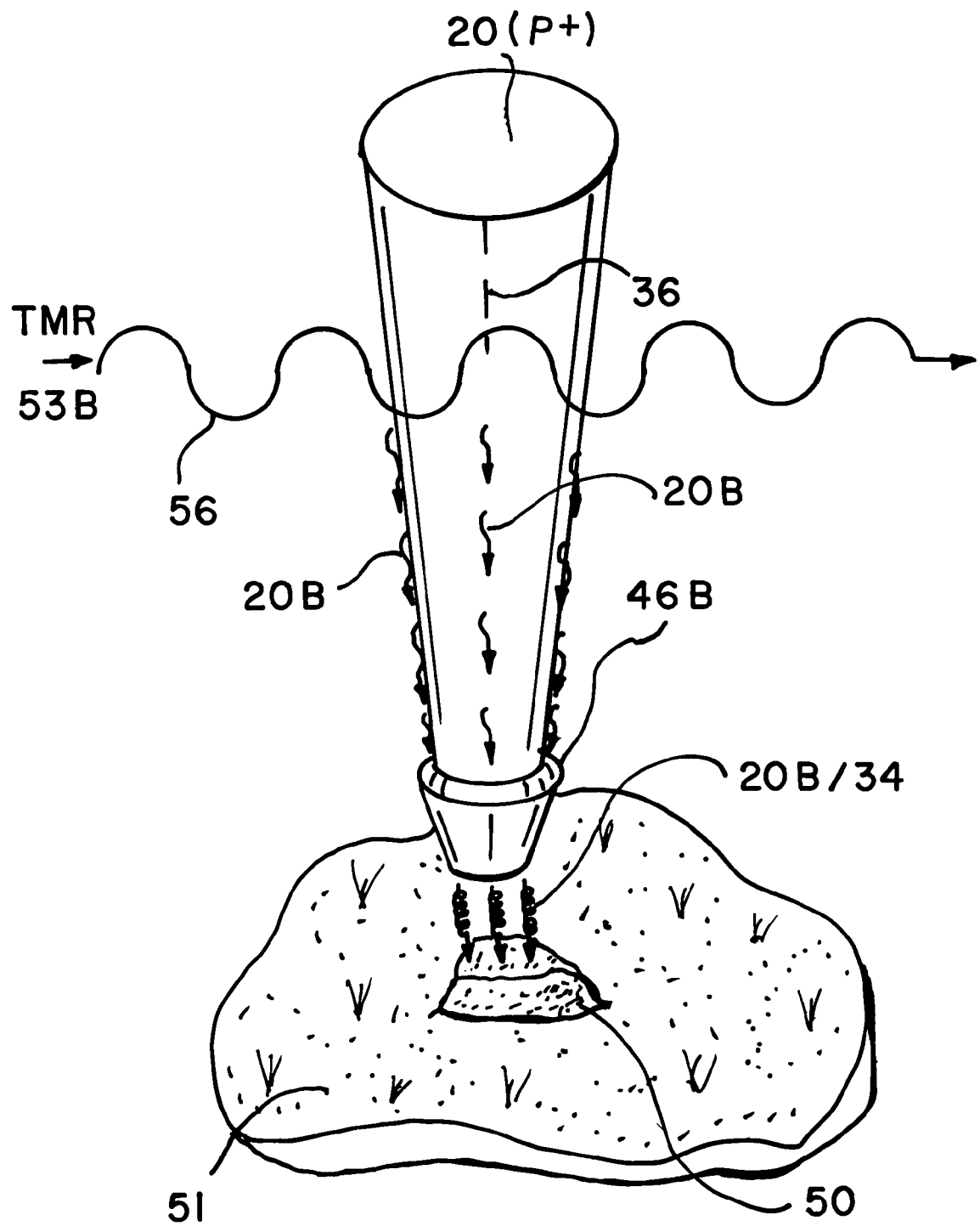
FIG. 5 is a schematic view of an alternative embodiment of that of FIG. 2 in which the TMR is applied ex vivo in order to impart its magnetic field patterns to the electrical energy and magnetic dipole spin to the proton beam, producing a resultant magnetic dipole moment to the protons of the proton source.

In FIG. 5 is shown another embodiment 55 of the inventive (method, alternative to that shown in FIG. 2) in which a TMR wave 56 generated by TMR generator 53B is shown. Therein, a TMR wave 56 interacts ex vivo with proton beam 20 to modify the beam into a beam 20B having characteristics of TMR wave 56 induced thereinto by virtue of an ExB vector interaction between the electrical properties of beam 20 and the magnetic properties of wave 56. This process, it is believed, will permit the usage of reduced energy proton or X-ray input 20 while achieving a comparable or improved therapeutic result at target 50 of tissue 51, due to the inherent therapeutic benefits of electron and nuclear magnetic resonance therapy.

Figure 6:
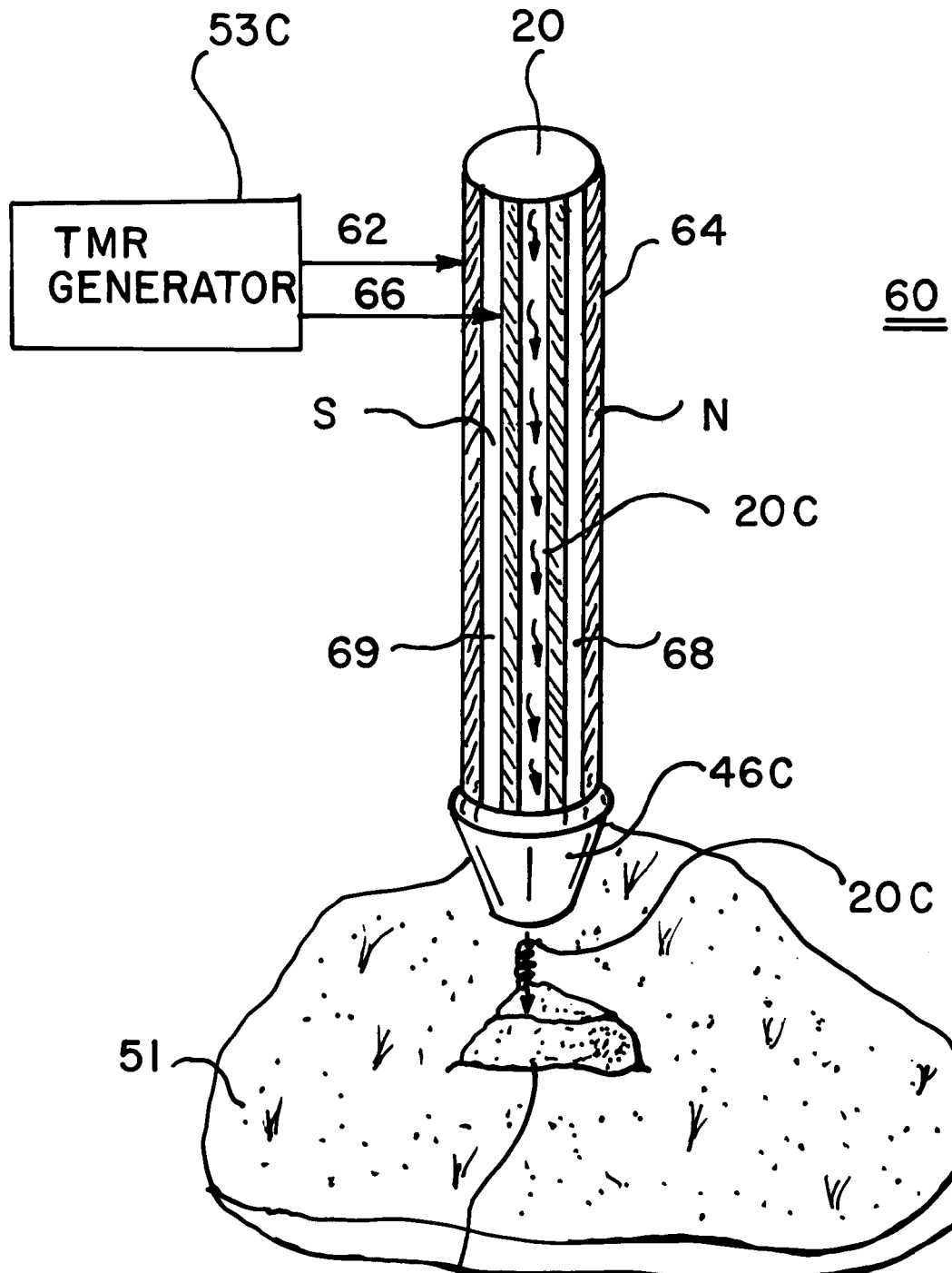
FIG. 6 is a further embodiment of the inventive method in which the TMR is applied to a coaxial waveguide in which the proton beam is delivered through an axial guide thereof thus imparting a magnetic spin to the protons delivered to the isocenter of therapy.

In FIG. 6 is shown a further embodiment 60 of the present inventive system and method in which a TMR generator 53C provides a magnetic north or positive output 62 to an outer coaxial waveguide 64 and provides a negative or magnetic south output 66 to an inner co-axial waveguide 68. The result thereof being an oscillating radial magnetic field in annular space 69 between the outer and inner coaxial waveguides 64 and 68 respectively, the result again, as in the case of the embodiment of FIG. 5, being a cross-vector interaction between the magnetic properties of the TMR field in region 69 and the electrical properties of proton beam 20, to produce a different beam 20C. As well, the inherent magnetic dipole moment of the proton will be effected by the field created in annular area 69 between the inner and outer coaxial waveguides, thus imparting some of the therapeutic properties of EMR or NMR therapy to the proton beam, and reducing the required input energy at source 20.

In FIG. 7 are shown the primary constituent subsystems of a EMR system 124, these including a microcontroller 149 having local treatment controls 132, a display 134, status LEDs 135, a memory 150 used for purposes of recording data, and a DC to DC converter 152. As may be noted, the output of converter 152 feeds into a pulse generator and level shifting means 154 which include current and voltage limiting means. The output of said means 154 is provided to means 156 for the simultaneous sensing of voltage and current associated with skin and tissue measurements. The output thereof is provided to said microcontroller 149 which operates with PC 112 through a radio interface unit 124. The system 124 also includes a battery pack 158 and its charger 160.

Inputs to probes (or induction coils) 53 and 55 are provided through said dual voltage and current sensing means 156. It is noted that there are two areas in which magnetic resonance fluxuation is measured. The first is through induction coil 52 and the second is through a treatment measurement probe 53. The more phase shift (disorder or loss of electron energy), the lower the measured amplitude and the greater the electromagnetic flux therethrough. See FIGS. 11/12.

Figure 8:
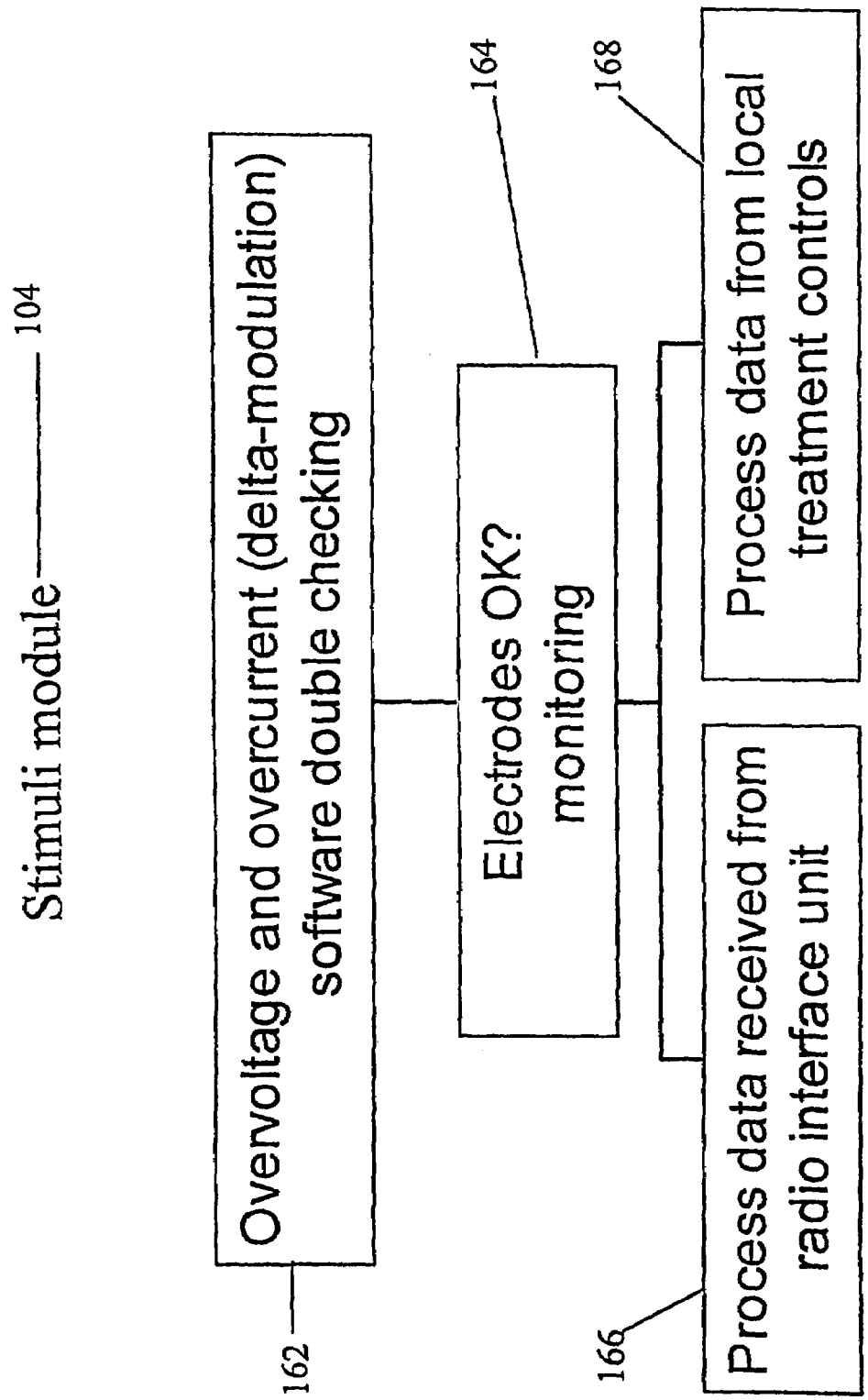
FIG. 8 is a block diagram view of a module that could be applied at the isocenter of therapeutic treatment.

In FIG. 8 is shown stimuli module 104 and, more particularly, over voltage and over-current software monitoring means 162, associated electrode or induction coil monitoring means 164, and associated RF means 166 for processing data received from radio interface unit 124, and means 168 for processing data from local treatment controls 132.

Figure 15:
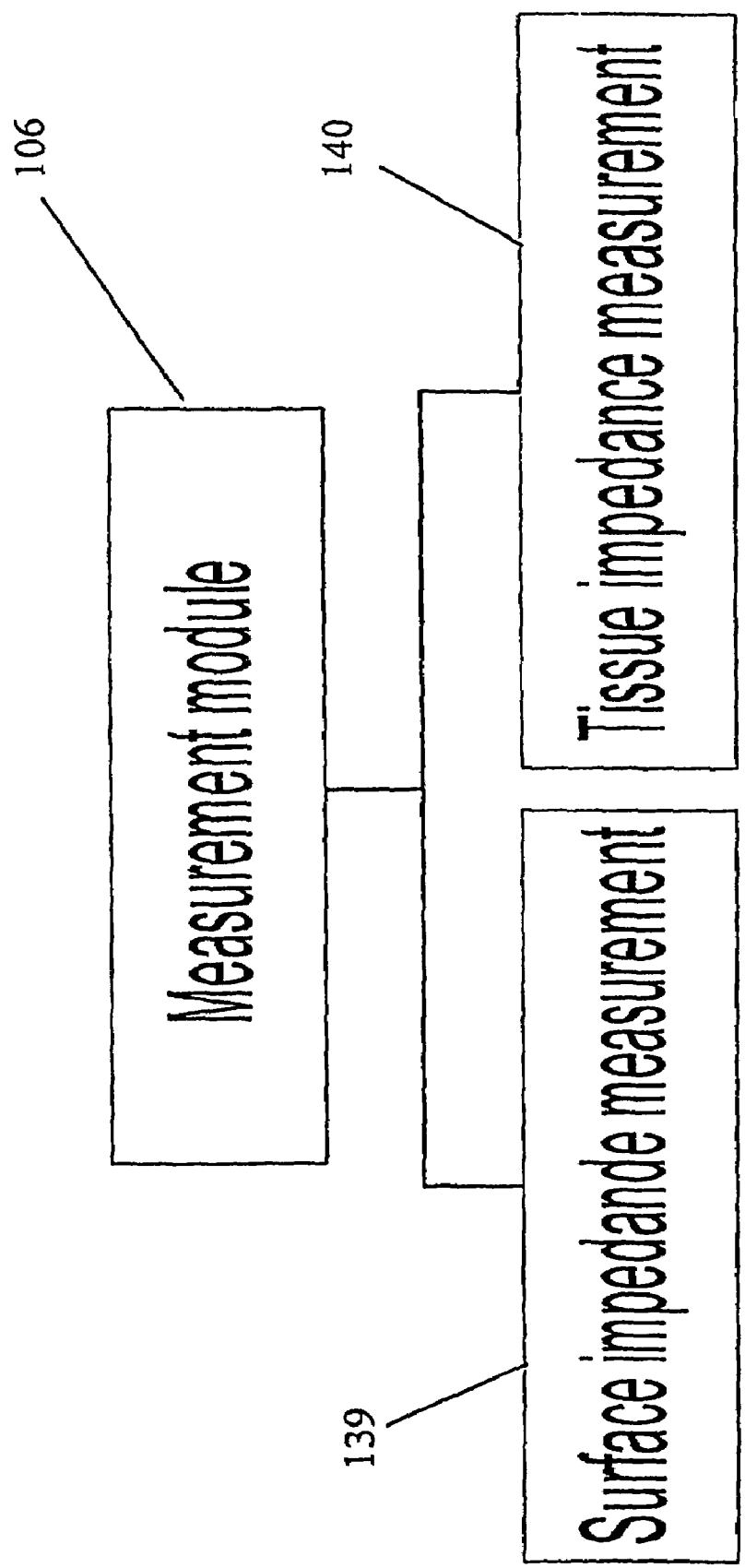
FIG. 15 is a block diagram view of the tissue impedance measurement assembly of the EMR.
Figure 16:
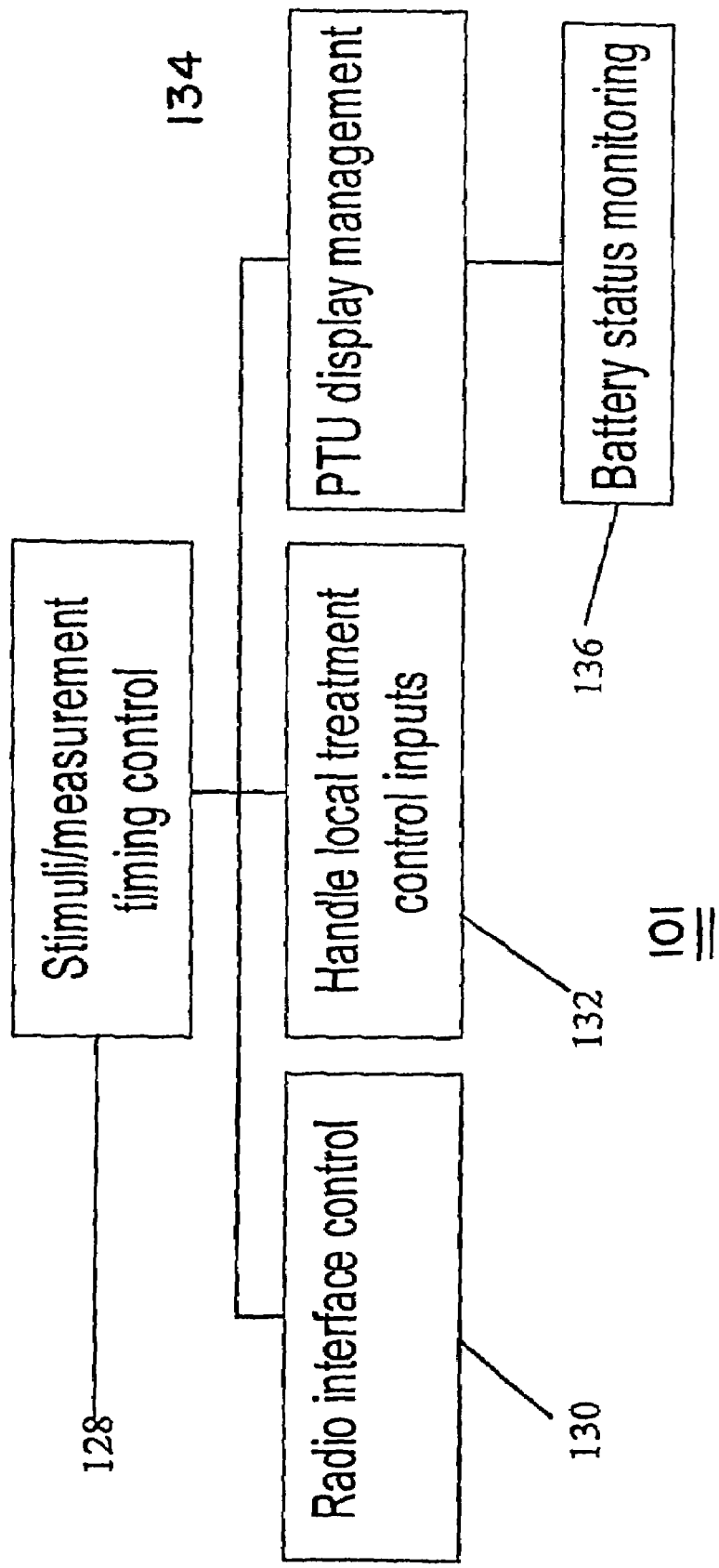
FIG. 16 is a block diagram view of the EMR patient treatment assembly with RF interface.

It is to be appreciated that electrodes associated with probes 53/55 and pad 116, that is, two electrodes connected via wire, one of which electrodes is provided with a linear potentiometer are used to adjust or select the intensity of the energy provided to the treated tissue 50. A number of safety features are incorporated into the instant system including visual and/or audio warning means, amplitude limit means (per block 156), amplitude override means, amplitude ramp back means, and patient control means. Therein data transmitted from functional management unit 101 to the system 51 includes stimuli frequency, stimuli duty cycle, and other patient threshold information (based upon patient history) to thereby optimize patient-side intensity settings. Data transmitted between the PTU and FMU include skin voltage, electromagnetic fluxuation and current phase (see FIG. 15) between skin and voltage current, tissue voltage and current, phase between tissue voltage, electromagnetic flux and current, and stimulus on/off status (see FIG. 16). It is noted the TMR system 51 may be in an EMR or NMR system.

Figure 17:
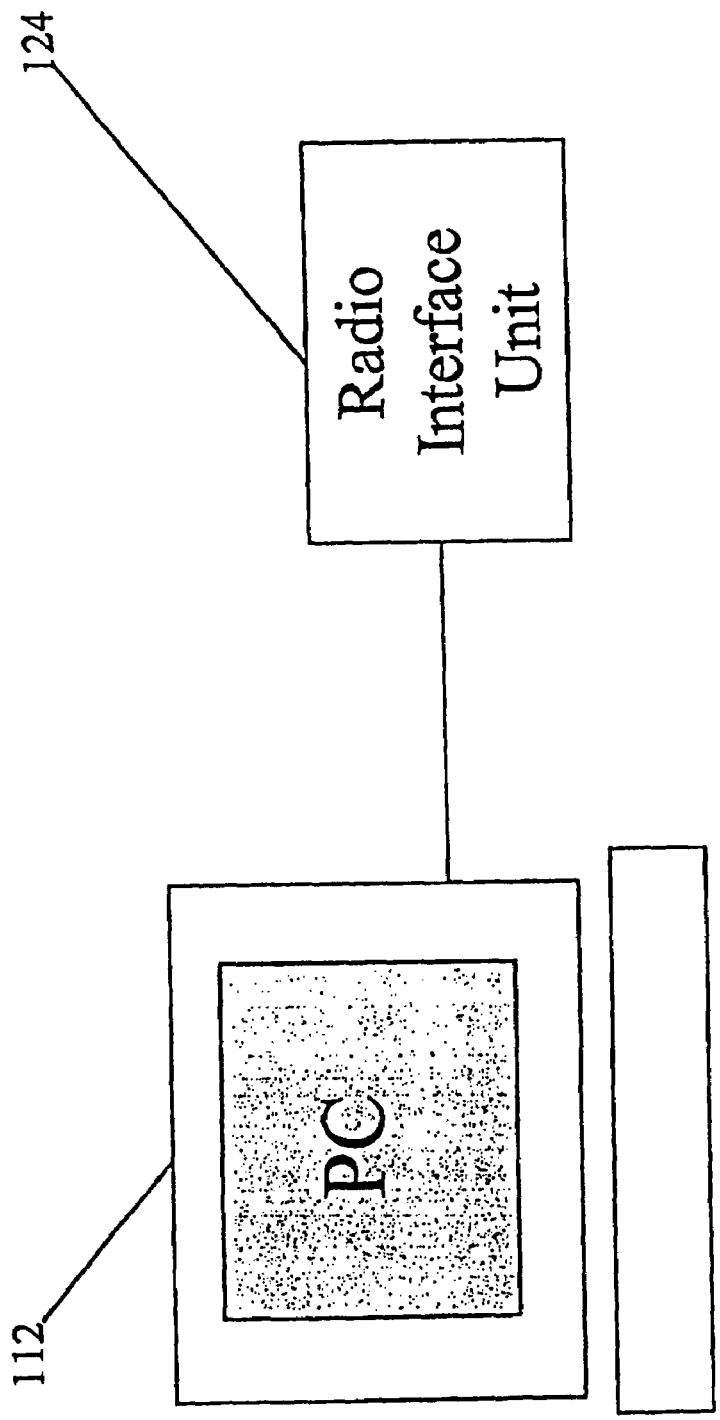
FIG. 17 is a view of a PC to RF interface of the EMR assembly.

Importantly, the local controller (see FIG. 17), if the EMR system is used employs various AI algorithms, i.e., the LC tuning of the EMR system employs various algorithms, starting with a so called inverse wave form of the injury tissue as a first order basis of treatment, this to be followed by robust stochastic models to generate appropriate stimuli profiles to enable the FMU 101 to provide a sophisticated treatment or correction signal. Therein at least three models or algorithms are contemplated, these including the following:
  sequential, adaptive self-learning method and implementation (for a single electrode pair);
  block adaptive self-learning method and implementation (for an electrode array);
  one and multi dimensional neural network-based controller algorithms;
  sequential data autoregressive method and implementation (for a single electrode pair); and
  block data autoregressive method and implementation (for an electrode array)

In addition, the filtering of the measurement module of the FMU eliminates error signals which typically appear as waveform ripples, to thereby enable generation of a correction or treatment signal from a self-learning multi-electrode PTU, thereby having enhanced efficacy in the cancellation of pain and, ultimately, long term treatment of the condition of interest.

Combinations of algorithms may be employed to generate interchannel waveform correlations to ensure convergence of the model analysis and promotion of its learning curve for the modeling of the tissue injury, treatment profiles and peak resonances associated therewith.

In summary, the EMR technology employ a frequency of 1 Hertz to 1 G hertz, and 0.1 to 10 Tesla in treatment signals to increase, decrease, flatten or nullify out of phase resonance peaks of a measured waveform of the tissue to be treated. Similarly, the correction or treatment signal which is applied to treat the abnormal tissue signal obtained by the measurement module is intelligently developed by a self-learning multi-electrode PTU in which various heuristic algorithms are used to ensure convergence and efficient development of models necessary to optimize tissue profile, peak resonance codes, and the use of this information for effective therapy in an array of medical conditions.

A library of tissue profiles and peak resonance codes may be employed in the system in the development of a separate library of profiles and EMR resonance codes for each patient and, also, as a baseline/or electromagnetic structures, of healthy tissue of many types, which might be employed in the generation of an inverse waveform (see discussion of FIGS. 13-14 below) or treatment purposes. Accordingly, an historic library of tissue profiles and peak resonance codes may be intergraded into the stochastic models, as set forth above, to generate appropriate stimuli profiles to enable a sophisticated treatment or correction signal. Therein a simple low-order low pass filtering process, to eliminate signal ripples, constitutes a starting point.

The next step is typically the generation of the inverse waveform or inverse EMR spectra which is a generation of an opposite magnetic single pattern from that shown in FIGS. 11 and 12. The application of this inverse pattern, has a pulse width modulation (PWM) process imposed upon a "sick" signal of the abnormal tissue is shown in FIG. 13. Thereby the system generates and applies to such tissue, a waveform of EMR peak spectra substantially inverse to that of out-of-phase resonances of said tissue signal to thereby increase or nullify EMR peaks of the signal associated with abnormalities. See FIG. 14.

The elements of the TMR system may be summarized as follows: (a) means for modulating a magnetic field having a strength, of between about 0.1 gauss and about 10 Tesla, across an RF spectrum of between about 1 Hz and about 1 GHz; (b) means for subjecting said tissue to said modulated magnetic field; (c) means for measuring resultant electron magnetic resonance (EMR) peaks of a signal emitted by said tissue, in which each peak of said EMR peaks represent either an in-phase or out-phase EMR; and (d) means for generating and applying to said tissue a waveform substantially inverse to that of said out-of-phase resonance of said EMR tissue signal, to thereby increase, decrease or nullify abnormal EMR peaks of said signal associated with said abnormality of said tissue.

Figure 18:
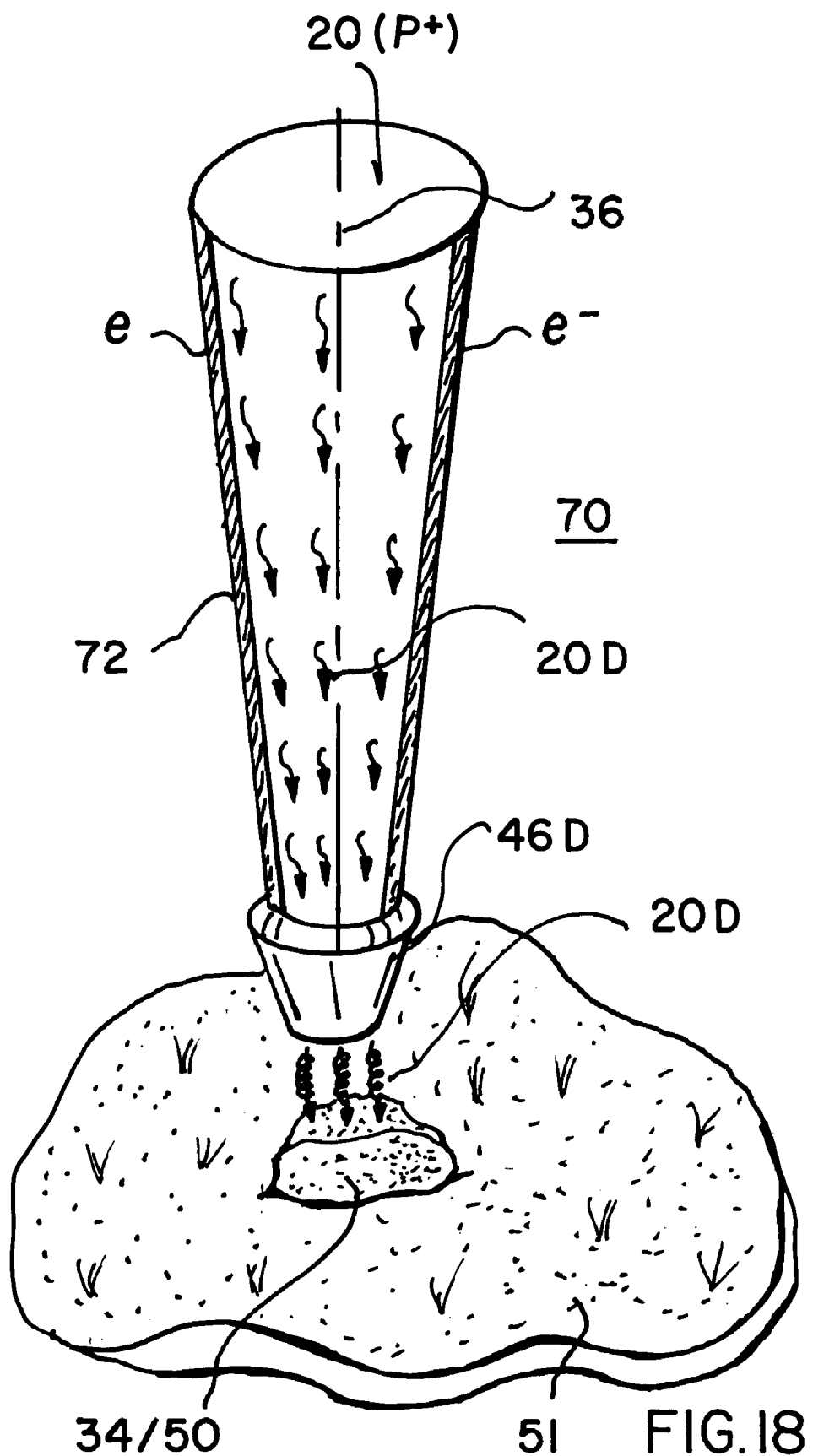
FIG. 18 is a schematic view of a further embodiment of the invention in which an electrically charged conical waveguide is used to retard the velocity or alter the pathway of protons emitted from the proton source.

Shown in FIG. 18 is a further embodiment 70 of the present invention in which there is employed a conical waveguide 72 which is electrostatically charged, the effect thereof being to retard the velocity of the proton beam 20. In a variant thereof, a sinusoidal, alternating or intermittent electrical signal may be applied to waveguide 72 to influence the electrical dipole moment of proton or x-ray 20, producing a modified treatment wave 20D.

Figure 19:
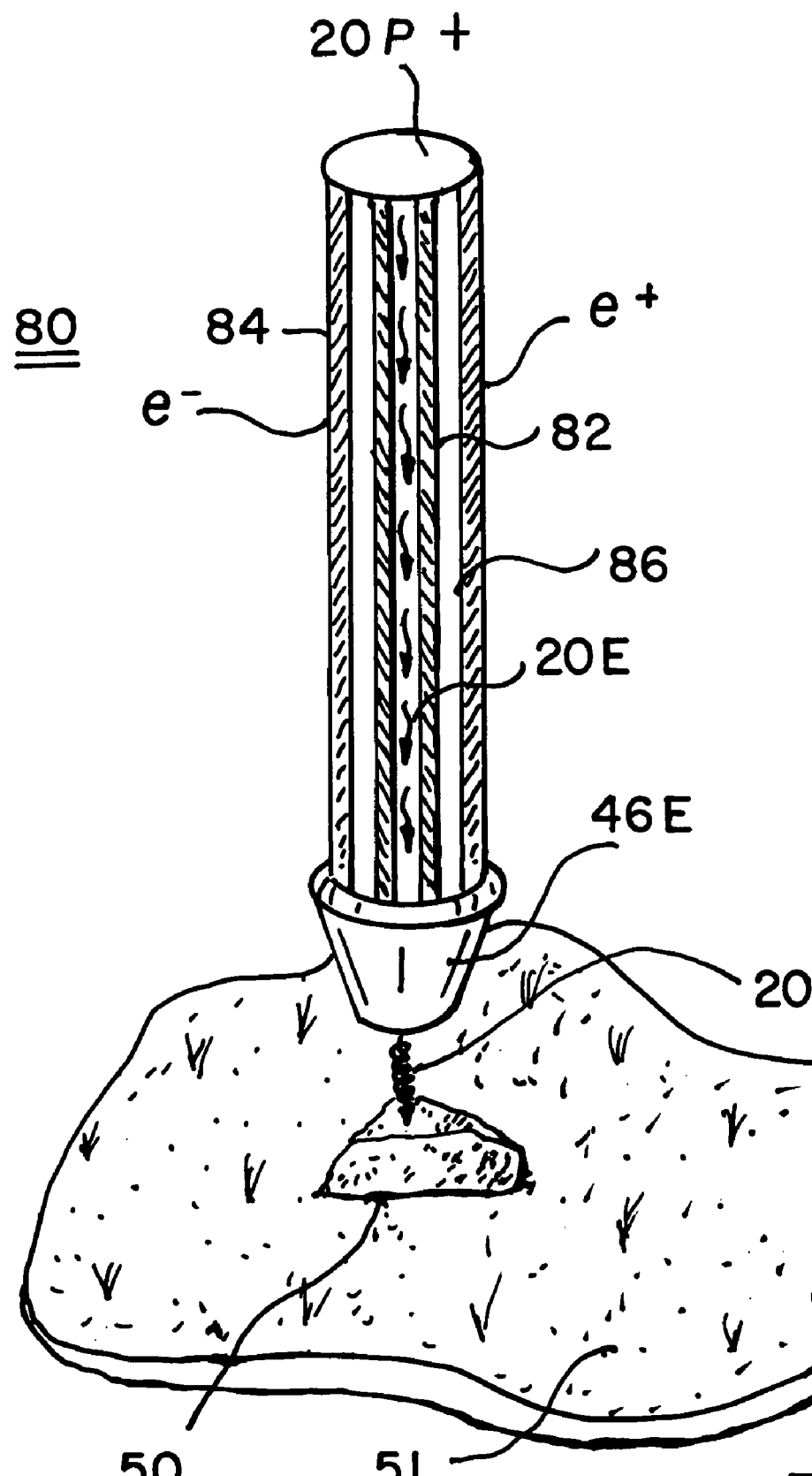
FIG. 19 is an embodiment, using the same principles as the embodiment of FIG. 18 in which a co-axial waveguide is employed to electrically retard the velocity or alter the pathway of emitted protons.

In FIG. 19 is shown a variation of the embodiment of FIG. 18 in which however an electrical field or waveform is applied between inner and outer waveguides 82 and 84 respectively to produce an oscillating electrical field within annular channel 86 between the respective waveguides, this in turn, to induce a modification of the electric dipole moments of the protons of radiation beam 20, producing an electrically modified beam 20E that is applied through a collimator 46E to the target 50.

Figure 20:
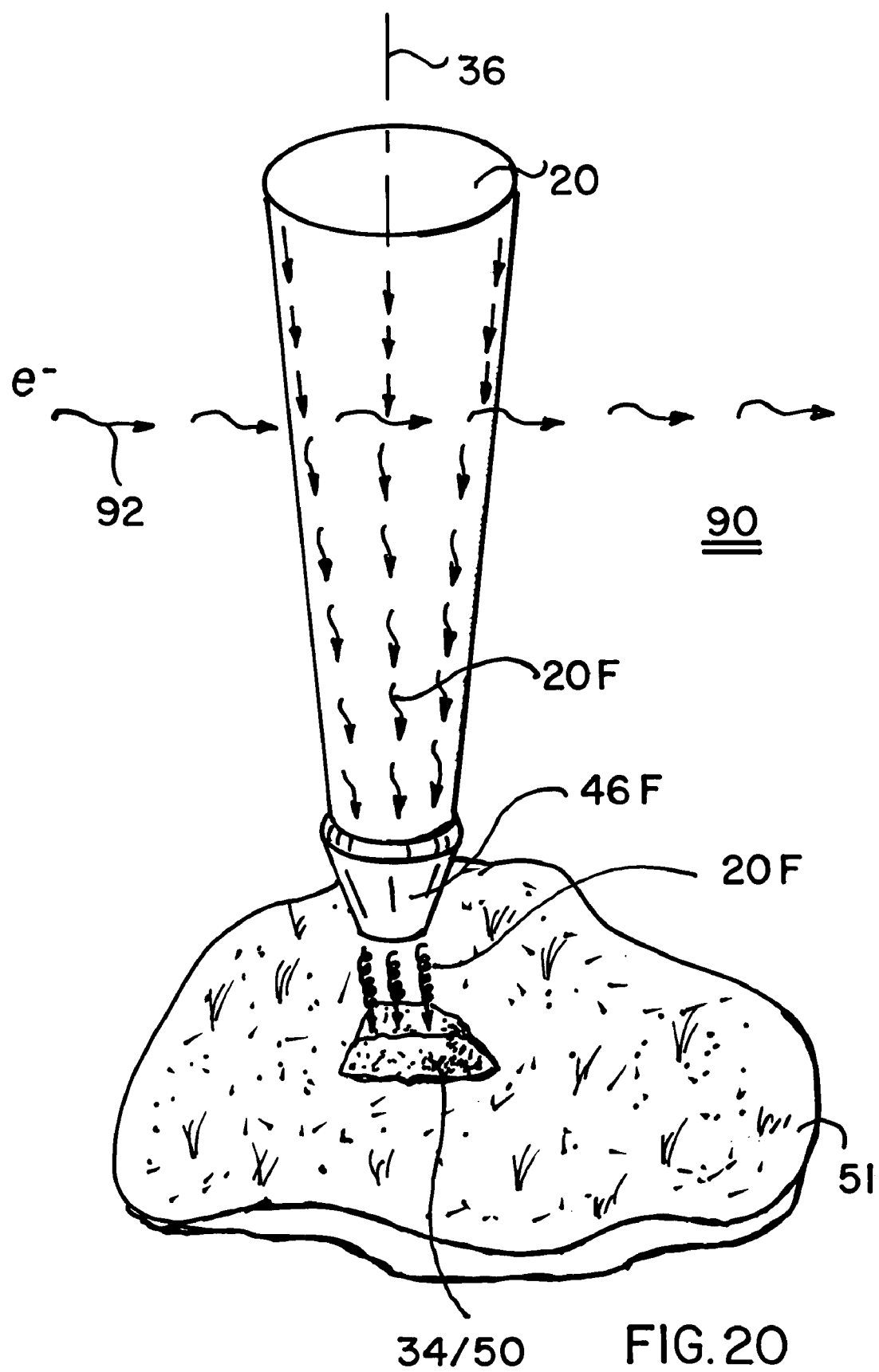
FIG. 20 is a schematic of a further embodiment of the invention in which an electron beam is provided at an angle to that of source beams to provide an ExB vector having a spiral shape reflective of the frequency, direction and energy of the electron beam, to retard the velocity of the proton beam and to modify the magnetic properties thereof.

Another strategy for altering the electric dipole moment of beam 20 is shown in an embodiment 90 of FIG. 20. Therein an electric signal 92 passes transversely, or at an angle, relative to the radiation axis 36 of the system.

Figure 21:
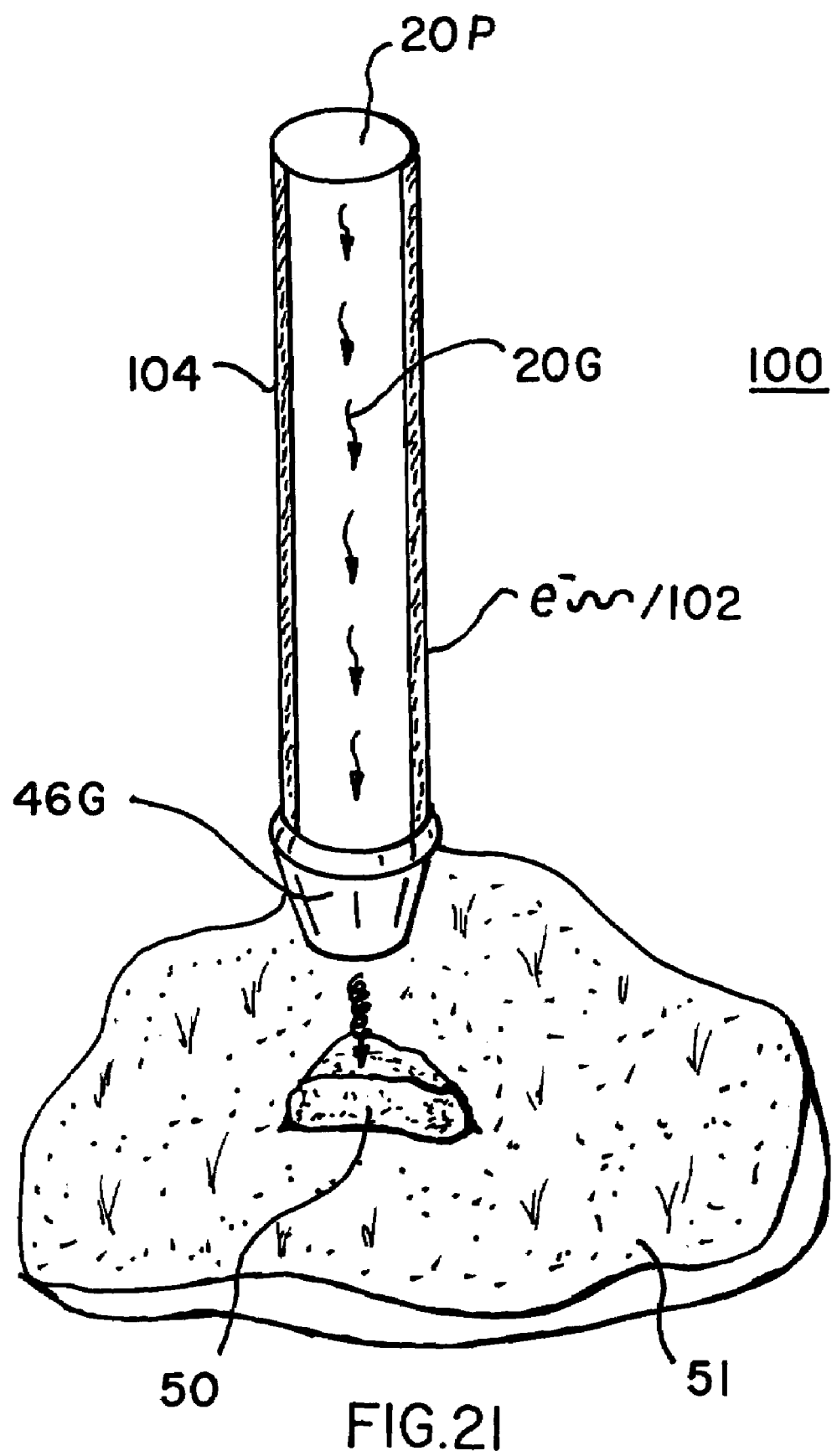
FIG. 21 is an embodiment employing a longitudinal capacitor to modify the velocity and pathway of the proton beam.

A further variant of the embodiments of FIGS. 19 and 20 is shown in embodiment 100 of FIG. 21 in which an oscillating signal 102 is applied to a cylindrical waveguide 104 or, in an alternate embodiment thereof, FIG. 21 may be considered as a longitudinal cross-sectional view of an AC capacitor in which the field strengths between opposite plates 105 and 107 thereof vary as a function of time and space, as may be dictated by therapeutic needs of the patient to produce a modified beam 20G.

Figure 22:
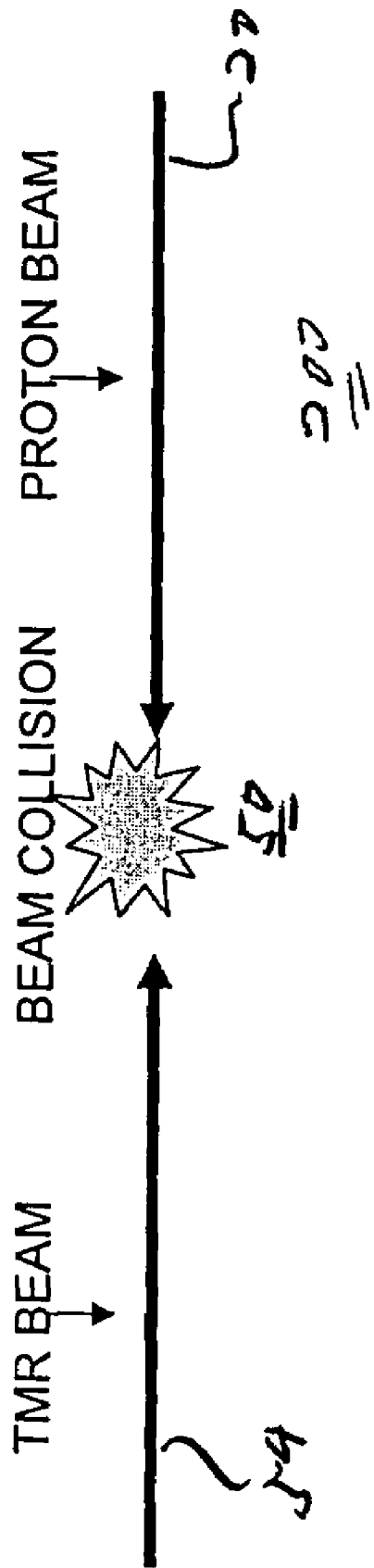
FIG. 22 shows a further embodiment in which the EMR and proton beam assemblies are directed at the target from opposite directions.

In FIG. 22 is shown an embodiment 200 that would use two coaxial guides at 180 degrees to each other one proton and one TMR aimed at each other with the lesion in the middle.

While there has been shown and described the preferred embodiment (FIG. 2) of the instant invention it is to be appreciated that the invention may be embodied otherwise than is herein specifically shown and described and that, within said embodiment, certain changes may be made in the form and arrangement of the parts without departing from the underlying ideas or principles of this invention as set forth herein.

The invevention claimed is:

1. A method of therapeutic treatment, comprising the steps of:
    (a) application of a time domain proton beam to a therapeutic target; and
    (b) a time domain application of a modulated—electron—magnetic resonance signal (—E—MR) to said therapeutic target during periods of beam application a least partially out-of-phase with energy peaks of said proton beam, In which said —E—MR signal defines a wave form substantially inverse to that of a stand-alone MR response associated with tissue abnormality of said—therapeutic target,—to thereby increase, decrease or nullify abnormal MR peaks of said stand-alone response thereof.

2. The method as recited in claim, 1, in which said time domain application of MR signal relative to energy peaks of said radiation beam comprises:
    substantially out-of-phase application thereof.

3. A method of therapeutic treatment, comprising the steps of:
    (a) application of—either—a time domain—proton beam or X-ray beam—to a therapeutic target; and
    (b) a time domain application of a modulated electron magnetic resonance signal (EMR) to said therapeutic target during periods of beam application a least partially out-of-phase with energy peaks of said proton beam, In which said EMR signal defines a wave form substantially inverse to that of a stand-alone MR response associated with tissue abnormality of said—therapeutic target,—to thereby increase, decrease or nullify abnormal MR peaks of said stand-alone response thereof.

4. The method as recited in claim 3, in which said modulated time domain application of said EMR signal relative to energy peaks of said radiation beam comprises:
    substantially out-of-phase application thereof.

* * * * *